United States Patent [19]

Pao

[11] Patent Number: 4,805,616
[45] Date of Patent: Feb. 21, 1989

[54] BIPOLAR PROBES FOR OPHTHALMIC SURGERY AND METHODS OF PERFORMING ANTERIOR CAPSULOTOMY

[76] Inventor: David S. C. Pao, 95 High Point Dr., Churchville, Pa. 18966

[21] Appl. No.: 933,026

[22] Filed: Nov. 20, 1986

Related U.S. Application Data

[60] Continuation-in-part of Ser. No. 690,266, Jan. 10, 1985, Pat. No. 4,674,459, which is a continuation-in-part of Ser. No. 611,967, May 18, 1984, abandoned, which is a division of Ser. No. 428,849, Sep. 30, 1982, Pat. No. 4,476,862, which is a division of Ser. No. 213,861, Dec. 8, 1980, abandoned, which is a continuation of Ser. No. 900,422, Feb. 5, 1979, abandoned.

[51] Int. Cl.$^4$ .............................................. A61B 17/39
[52] U.S. Cl. .............................................. 128/303.17
[58] Field of Search ...................... 128/303.13, 303.14, 128/303.17, 303.18, 303.19

[56] References Cited

U.S. PATENT DOCUMENTS

| | | | |
|---|---|---|---|
| 1,814,791 | 7/1931 | Ende | 128/303.17 |
| 1,983,669 | 12/1934 | Kimble | 128/303.17 |
| 2,275,167 | 3/1942 | Bierman | 128/303.17 |
| 3,651,812 | 3/1972 | Samuels | 128/303.18 |
| 3,920,021 | 11/1975 | Hiltebrandt | 128/303.17 |
| 3,974,833 | 8/1976 | Durden | 128/275.1 |
| 3,987,795 | 10/1976 | Morrison | 128/303.14 |
| 4,034,762 | 7/1977 | Cosens et al. | 128/303.17 |
| 4,103,688 | 8/1978 | Edwards | 128/303.17 |
| 4,301,802 | 11/1981 | Poler | 128/303.14 |
| 4,476,862 | 10/1984 | Pao | 128/303.17 |
| 4,483,338 | 11/1984 | Bloom et al. | 128/303.13 |
| 4,548,207 | 10/1985 | Reimels | 128/303.17 |
| 4,565,200 | 1/1986 | Cosman | 128/303.18 X |

FOREIGN PATENT DOCUMENTS 2101893A 1/1983 United Kingdom .

OTHER PUBLICATIONS

Pao, "Coaxial Bipolar Probe", Archives of Ophthalmology, Jul. 1979, vol. 97, pp. 1351-1352.
Bipolar Forceps for Electrocautery Tonsillectomy, Reed et al., Transactions of AAOO, vol. 78, 1974.
Bipolar Journal of Ophthalmic Operations, McPherson, Jr. American Journal of Ophthalmology, vol. 73, No. 5, May 1972.
Decker et al., "An Electrocautery Instrument..." 10th Annual Rocky Mountain Bio. Eng. Symposium, Boulder, Colo., May 7-9, 1973.
Schmidt et al., "Vas Cautery...", Urology, vol. III, No. 5 May 1974, pp. 604-605.
"Spot Electrocautery with Coaxial Bipolar Probe" *Ophthalmology Times*, Jul. 1978.
Dr. Drew, Wet-Field Cautery Tip Works Like Pencil Erasure, IOL Ocular Surgery News, Oct. 15, 1983 edition.
Mentor O&O, Inc. Hemostatic Erasure Mentor's New Wet-Field* Disposable Erasure, AJO Jul. 1983.
Mentor O&O, Hemostatic Erasure, Now pinpoint control of retinal as well as anterior chamber bleeders. Source (unknown), published by Jan. 10, 1984.
Peyman et al., "Experimental Intraocular Coagulation," *Ophthalmic Surgery, vol. 3, No. 1, Jan.-Feb. 1972.*

*Primary Examiner*—Lee S. Cohen
*Attorney, Agent, or Firm*—Woodcock Washburn Kurtz Mackiewicz & Norris

[57] ABSTRACT

A bipolar probe device for ophthalmic surgery such as anterior capsule cutting includes an elongated probe electrode assembly having an active tip region where a pair of electrodes are exposed along a sidewall portion of the active tip region such that there exists a single axis of closest approach between the two exposed electrodes which lies along the side of the probe. The preferred embodiment includes an outer cylindrical metal tube electrode forming the outer surface of the elongated probe and a axial electrode coaxial with the tubular electrode at the extreme tip of the tubular electrode and extending from the tubular electrode and radially away from the central axis of the tubular electrode to one side of the probe. The central axis of the extreme tip of the central electrode is turned away at least 45° and suggestedly about 80° and 90° from the central axis of the tubular member. In another embodiment, a pair of electrode tips are exposed through the surface of a hemispherical insulator supported by a tubular member on one side of a central axis through the insulator hemispherical surface and the tube, coplanar with that central axis.

9 Claims, 3 Drawing Sheets

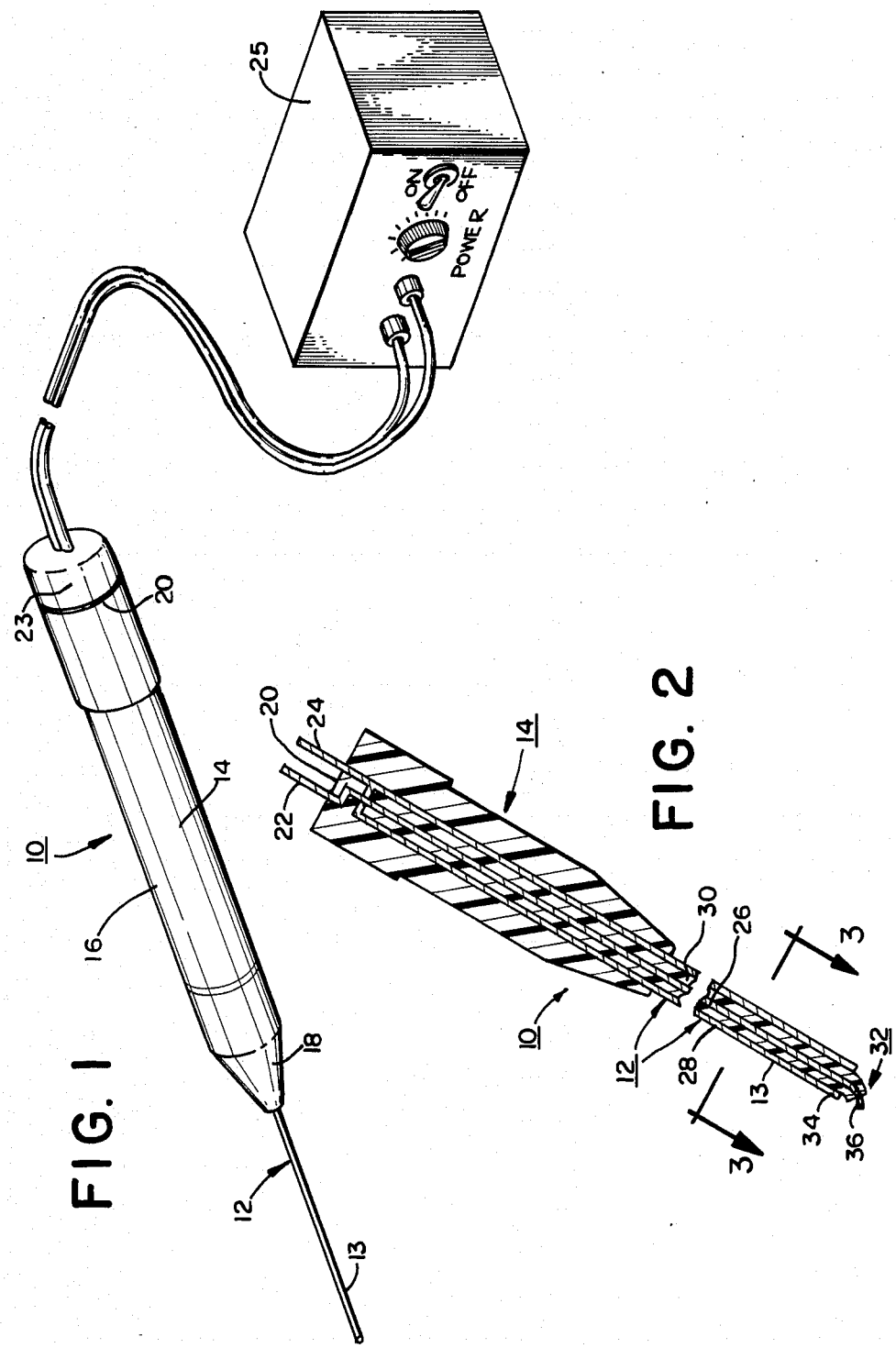

BIPOLAR PROBES FOR OPHTHALMIC SURGERY AND METHODS OF PERFORMING ANTERIOR CAPSULOTOMY

This is a continuation-in-part of Ser. No. 690,266 filed Jan. 10, 1985, now U.S. Pat. No. 4,674,499, a continuation-in-part of Ser. No. 611,967, filed May 18, 1984, now abandoned, which was a division of Ser. No. 428,849, filed Sept. 30, 1982 and now U.S. Pat. No. 4,476,862, which was a division of Ser. No. 213,861 filed Dec. 8, 1980, now abandoned, which was a continuation of application Ser. No. 900,422 filed Feb. 5, 1979, now abandoned, all of which are incorporated by reference.

FIELD OF THE INVENTION

This invention relates to electrical surgical devices and, in particular, to bipolar probe devices for use in anterior capsulotomy procedures and other ophthalmic electrocautery and/or electrocoagulation procedures. One skilled in medical arts will appreciate that the coagulation of protein is a precurser to cauterization of tissue. The use of word cautery or similar words hereinafter with respect to the subject invention will be understood to encompass coagulation, where that operation is also appropriate.

BACKGROUND OF THE INVENTION

Bipolar devices are, by now, well known for use in ophthalmic and other surgical procedures. Such devices include two isolated electrodes which are placed in contact with a field of tissue to be treated. The electrodes are coupled with a power supply which passes an electric current through the electrodes and tissue contacted by the electrodes.

Applicant's U.S. Pat. No. 4,476,862, identified above, describes an earlier bipolar probe device and its use for scleral marking. The described embodiment includes a coaxial bipolar electrode assembly with an outer tubular electrode coaxially surrounding an inner axial electrode. The working tip of the probe device may be bent away from a center line of the major portion of the coaxial assembly for ease of use but remain coaxial at the tip which is applied to the tissue field. In the described embodiment, current flows uniformly in all radial directions between the axial electrode and the coaxial surrounding tubular electrode. This configuration provides a rapid reduction of the current density away from the axial electrode, and allows the generation of a small uniform charpoint in the sclera without cutting through the sclera.

Another bipolar ophthalmic device in U.S. Pat. No. 4,548,207 to Reimels includes a probe electrode assembly with a tubular outer electrode and coaxial central electrode. The end of the probe is beveled at an angle of about 45° to the central axis of the probe assembly. The central electrode is relatively large in comparison to the overall electrode assembly and effectively reduces current density around the central electrode. This device is designed particularly for coagulation of blood vessels and/or tissue and is less apt to cauterize sufficiently to cut than is applicant's own earlier embodiments.

U.S. Pat. No. 4,301,802 to Poler describes a cauterizing tool for ophthalmic surgery including anterior capsulotomy. The tool is provided by means of a modified hypodermic syringe needle. The tip of the needle is turned at an approximately 90° angle. An insulated fine wire is passed through the needle portion and turned tip and protrudes substantially coaxially with the end of the turned tip. Like the previous devices, current density would be concentrated around the central electrode but drop away substantial uniformly in all radial directions because of the coaxial orientation of the surrounding electrode formed by the needle.

U.S. Pat. No. 4,483,338 to Bloom et al and related UK application GB No. 2 101 893 describe yet another bipolar electrocauterizing needle embodiment including a perfectly straight outer cylindrical electrode and a coaxially positioned inner electrode. The end of this bipolar electrode needle may be conical frustoconical or perfectly blunt. These would all appear to provide uniform radial current densities around the center electrode.

A number of other references disclose similar, uniformly radially symmetric tubular outer electrode and coaxial inner electrode assemblies. See, for example, "Experimental Intraocular Coagulation", *OPHTHALMIC SURGERY*, January-February 1972, Vol. 3, No. 1 pp. 32-37; U.S. Pat. No. 2,275,167 to Bierman; U.S. Pat. No. 4,034,762 to Casens et al; "Vas Cautery: Battery - Powered Instrument For Vasectomy", Schmidt et al, *UROLOGY* Volume III, No. 5, May, 1974, pp. 604–605; An Electro Cautery Instrument For The Fulguration Of The Vas Deferens During Vasectomy For Sterilization", Decker et al, "ISA REPRINT, ISA BM 73302, pp. 5–10, 1973. The latter three references relate to devices inserted into the male vas for sterilization. In each of these devices, as with those previously mentioned, a tubular electrode and coaxially located central electrode is provided causing the aforementioned rapid reduction in current density substantially uniformly around the central, axial electrode.

Other bipolar probe configurations are known. For example, U.S. Pat. No. 3,920,021 to Hiltebrandt has, in addition to a coaxial concentric configuration like those previously discussed, several embodiments in which the center electrode mushrooms from the end of a tubular electrode in a hemispheral dome having an outer diameter equal to that of the tubular electrodes. Such a large "central" electrode would appear to reduce current densities even more than previously discussed embodiments. Another bipolar electrode embodiment includes a pair of semi-circular electrodes. The cord side of the electrodes are adjoining and uniformly spaced from one another. This configuration provides a uniform current density over a relatively wide area between the cord surfaces and lesser current densities between the arcuate surfaces. U.S. Pat. No. 1,983,669 to Kimble teaches a similar configuration of different construction.

U.S. Pat. No. 1,814,791 to Ende describes a bipolar probe device with a pair of parallel spaced axially extending electrodes which can be exposed to varying degrees for different lengths of cervical canal coagulation. It is believed that a substantially uniform current density is also provided between the exposed lengths of electrode.

Lastly, U.S. Pat. No. 3,987,795 to Morrison describes a number of sesqipolar electrode devices particularly suited for cutting and heavy coagulation applications. Not only are these devices too large for ophthalmic use, the arcing they are designed to provide is likely to cause injury to the optic nerve and other tissue of the eye.

None of the foregoing configurations, is believed optimal for anterior capsule cutting. That procedure requires the provision of sufficient current density to coagulate the anterior capsule and, preferably, the immediately underlining cortex, but currents and voltages sufficiently small so as to avoid optic nerve and other undesired tissue damage.

SUMMARY OF THE INVENTION

It is a first object of the invention to provide a bipolar probe device having a configuration optimized for anterior capsule cutting.

It is yet another object of the invention to provide an improved bipolar probe configuration for anterior capsule cutting which is relatively easy to manufacture.

It is yet another object of the invention to provide a bipolar probe configuration to maximize electric current density in a relatively small area between the electrodes.

These and other objects are provided by an improvement for a bipolar probe device with bipolar electrode assembly which includes an elongated probe, a first electrode exposed in at least a tip region of the probe and a second electrode also exposed at the tip region and positioned asymmetrically with respect to the first exposed electrode to provide a single axis of closest approach between the two exposed electrodes which lies along one side of the probe. The preferred embodiment includes a first tubular electrode having a central axis at a first hollow tubular end thereof and a second electrode extending from said hollow tubular end of the first electrode and radially away from said central axis. A central axis of an extreme tip of the second electrode is turned at least about 45°, and preferably between about 80° and 90° from the central axis of the hollow tubular electrode. Suggestably, the diameter of the remote end portion of the second electrode is reduced, at least in the vicinity of the extreme tip of the electrode, to further maximize local current density. The diameter may be tapered sufficiently to reduce the extreme tip to a dull point. An insulating material sleeve also be provided separates said two electrodes along their coaxial length and including the first end of the tubular electrode and may extend from that first end covering part of the remote end portion of the second electrode. The extreme tip of the second electrode may also be turned sufficiently to extend even through the plane of the outer surface of the first electrode at its tubular end.

Other variations of these configurations are also described in claims.

BRIEF DESCRIPTION OF THE DRAWINGS

FIG. 1 depicts diagrammatically a bipolar probe device of the subject invention and connected bipolar power supply unit.

FIG. 2 is a diagrammatic longitudinal cross-section of the bipolar probe device of FIG. 1.

DETAILED DESCRIPTION OF THE INVENTION

Figure 3:
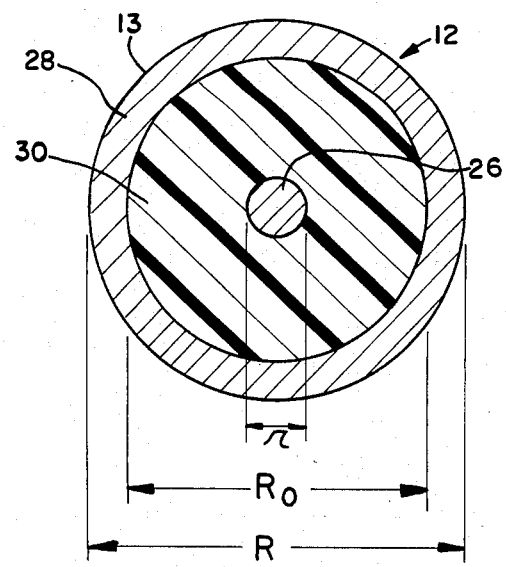
FIG. 3 is a diagrammatic transverse cross section of the remote active end of the bipolar electrode assembly along lines 3—3 of FIG. 2.

In FIG. 1 there is shown a preferred embodiment of a bipolar probe device of the present invention designated generally 10. The device 10 includes an elongate probe portion 12 with an circumferential outer side wall 13 disposed in an insulating hand piece portion 14. The hand piece 14 may be made of an electrically insulating polymetric material such as polytetrafluorothylene or polysulphone, configured in a pencil-shape form having a cylindrical body region 16 and a tapered forward region 18. Although the pencil-shape configuration is preferred, it is noted that any configuration of the hand piece portion 14 which is easily, comfortably and conveniently grasped by the surgeon will also be suitable and is considered to be within the scope of my invention. The opposing end 20 of the hand piece portion 14 is adapted for mating with a connector 23 from to the output terminals of a high frequency, bipolar power supply 25, preferably, a solid state unit having a bipolar output continuously adjustable between minimum and maximum power settings. A preferred bipolar power supply unit is manufactured by Grieshaber of Switzerland and distributed in the United States by Grieshaber. Another suggested unit, the Concept R bipolar coagulator, is distributed in the United States by the company of the same name. These devices are distinguished from older bipolar power supply units which are equipped with spark-gap circuits. The output of these older devices is a higher voltage, not as stable, subject to more surges than is the output of the suggested and preferred devices. The power surges and high voltage levels of the spark gap circuit equipped power supply units make uniform coagulation difficult to achieve and, at the power levels required for performing an anterior capsulotomy incision, may cause undesirable ionization and spark discharge at the probe tip which could damage the ocular structures.

Referring now to FIG. 2, the device of FIG. 1 is longitudinally sectioned to reveal its construction. The electrode probe assembly portion 12 includes a central or axial electrode 26 formed by a solid cylindrical metal member, and an elongate hollow outer electrode 28 formed by a cylindrical metal tube member, which is coaxially positioned around the central electrode 26. The cylindrical outer surface of electrode 28 forms the circumferential surface 13 of the probe 12. The outer electrode is preferably made of stainless steel or other corrosive resistant, conductive material for strength as well as conductivity. The inner electrode 26 may be made of copper but less conductive materials may also be employed. The coaxial relationship and spacing between the electrodes 26 and 28, as well as their electrical isolation from one another, is provided by a tubular sleeve of an electrically insulating material 30 between the electrodes 26, 28, such as polytetrafluoroethylene or polysulflone, completing the probe assembly 12.

The end region of the probe assembly 12 remote from the handle 14 constitutes an active region where the two conductive electrodes 26, 28 are exposed and is designated generally 32. The active region 32 includes a hollow tubular end with annular transverse end surface 34 of the outer electrode 28 and an end portion 36 of the central electrode 26 protruding from the end surface 34 of the outer electrode 28. Of course, the exposed outer cylindrical surface 33 of the outer electrode 28 is also conductive. A pair of pins 22 and 24 are exposed at the connection end 20 of the device for coupling the device with the power receptacle 23. The pins are electrically coupled with the axial and outer electrodes 26 and 28, respectively.

FIG. 3 depicts a transverse cross-section of the probe assembly 12. Maintaining a convention originated in the first of this series of applications, the diameter of the inner, central or axial electrode 26 is represented by the dimension "r" while the inner and outer diameters of the outer, hollow tubular electrode 28 represented by the dimensions "$R_o$" and "R" respectively. For ophthalmic procedures, it is suggested that the outer electrode 28 be formed from a 19 needle gauge size tube and, preferably, from a smaller diameter tube such as a 22 or 23 needle gauge size. Depending upon the diameter of the outer tubular electrode 28, the inner, axial electrode 26 might have a diameter ranging from 0.25 mm down preferably to between about 0.15 and 0.10 mm. The insulation sleeve 30 is of an appropriate size to fill the annular gap between the two electrodes 26 and 28.

Figure 4:
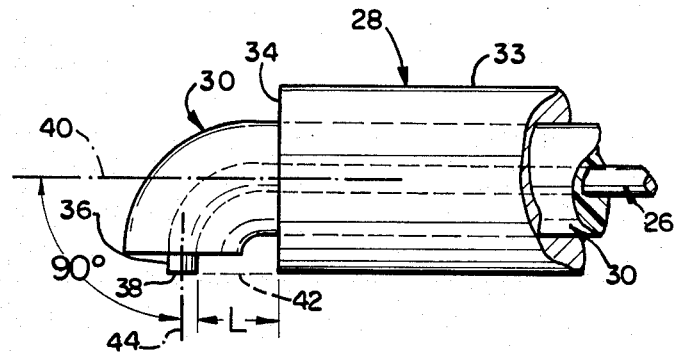
FIG. 4 is a diagrammatic side elevation of a first probe assembly tip configuration.
Figure 5:
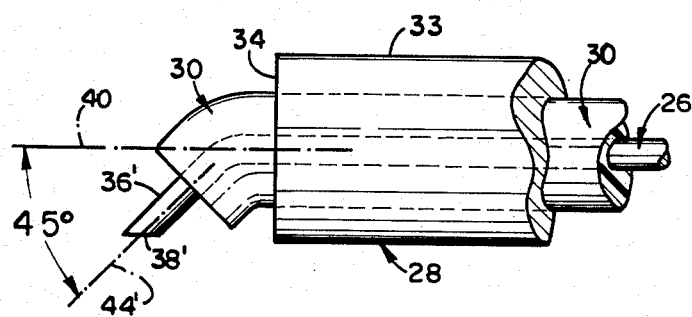
FIG. 5 is a diagrammatic side elevation of a second probe assembly tip configuration.

Referring now to FIG. 4, the end portion 36 of the axial electrode 26 projects beyond the end surface 34 at the remote end of the outer tubular electrode 28 sufficiently to allow it to be turned away from a central axis 40 of the outer electrode at its exposed end surface 34. The end portion 36 is extended sufficiently so that the extreme tip 38 of the central electrode 26 extends to or even slightly through a projection of the outer tubular electrode 28 indicated by broken line 42. The insulating sleeve 30 is also extended beyond the end surface 34 of the outer tubular electrode almost to the extreme remote tip 38 of the axial electrode 26 so as to insulate the majority of the projecting end portion 36 of that electrode and thereby concentrate current density between the tip 38 of that electrode and the outer electrode 28. In the embodiment of FIG. 4, the end portion 36 is turned sufficiently so that a central axis 44 of the electrode 26 at its tip 38 is substantially normal to the central axis 40, preferably forming an angle of approximately 80° to 90° with the aforesaid central axis 40. The radius of curvature applied to the projecting portion 36 of the central electrode 26 is as small as possible to minimize the distance L between the closest adjoining portions 34 and 38 of the electrodes 26 and 28, respectively. A single axis extends between the closest approaching points of the exposed surface of the end 34 of the outer electrode 28 and the exposed surface of the projection end portion 36 of the central electrode 26 and lies essentially along the side of the probe assembly 12 to which the portion 36 is turned. This single axis is also represented by line 42. The subject invention is unique in having only one such axis on a side of the probe. Preferably, the projecting portion of the insulating sleeve 30 is of a length sufficient to expose at least about 0.2 millimeters of the projecting end 36 of the central electrode 26, although less insulation or no projecting insulative sleeve may be provided. While about a 60°-90° angle turn in the central electrode 26 is desired and 80°-90° preferred, referring to FIG. 5, a central electrode 26 may be turned away from a central axis 40 of a coaxial tubular electrode 28 to a lesser amount. It is believed, however, that the central axis 44' of he central electrode 26' at tip 38' should be turned away from the central axis 40 at the end 34 of the tubular electrode 28 by at least about 15°. In FIG. 5, the tip 38' has been machined approximately parallel with central axis 40 to present an oval inner electrode surface substantially flush with the outer, cylindrical side wall 33 of the outer electrode 28. The oval shape is believed to assist in developing a more uniform current density around the tip 38' than would a surface perpendicular to the axial electrode centerline 44'.

Figure 6:
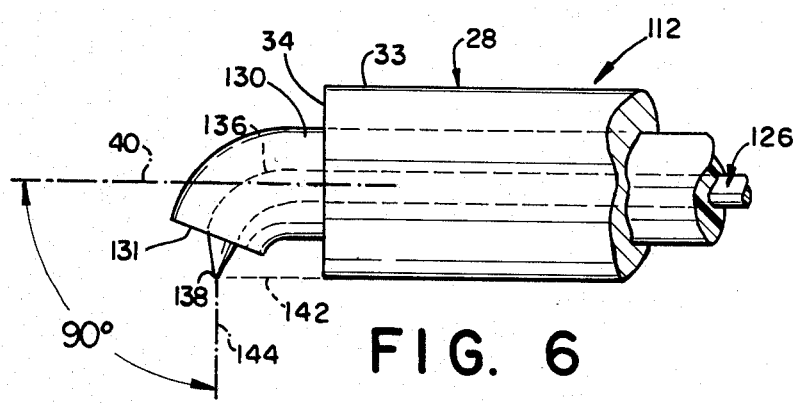
FIG. 6 is a diagrammatic side elevation of a third probe assembly tip configuration.

For greater current probe density, the probe configuration 112 of FIG. 6 is suggested. A remote end portion 136 of a central, axial electrode 126 protrudes from the end 34 of a cylindrical outer electrode 28 concentric with that electrode 28 and its central axis 40 at end 34. The central axis 144 at the tip 138 of the projecting portion 136 of the central electrode 126 is again turned away from the central axis 40 by as much as about 90°. Moreover, the diameter of the remote end portion 136 of the central electrode 126 is tapered as it extends from the surface 131 of the insulating sleeve 130 and terminates in a dulled (i.e. radiused) tip 138. Again, the tip 138 extends to or slightly through a projection, represented by broken line 142, of the cylindrical side wall surface 33 of electrode 28 at end 34. The insulative material sleeve 130 between the electrodes 126 and 128 preferably extends to within a few tenths of a millimeter from the tip 138 but may not extend at all beyond the end 34 of the outer electrode 28 or may extend only somewhat so as to not interfere with the reduction of the diameter and the bending of the remote end portion 136 of the axial electrode 126. In this way, current density between the remote end of the axial electrode 126 and the exposed surface of the outer electrode 128 is maximized by reducing the area of the tip end 138 of the axial electrode 126 contacting the patient. Although it is desired to maximize the current density at the tip of the center electrode, it is further desired that the density not be excessively distorted by extremely close proximity between the adjoining sides of the two electrodes. For larger probes (19 needle gauge outer electrode diameter, 0.25 mm inner electrode diameter) 0.7 mm spacing between the electrode tips has been employed with a 30° angle. It is envisioned that 0.50 to 0.25 mm spacing between electrode tips might be favorably employed with smaller probe assemblies (i.e. 22-23 needle gauge outer electrode diameters 0.10-0.15 mm axial electrode diameters) at larger angles.

The probe assembly portions of the embodiments of FIGS. 1-6 are configured by any of the methods conventionally employed to fabricate coaxial needle bipolar electrode assemblies such as by making such an assembly and thereafter processing the remote end tip by bending, machining, etc. to form to the configuration desire.

Figure 7:
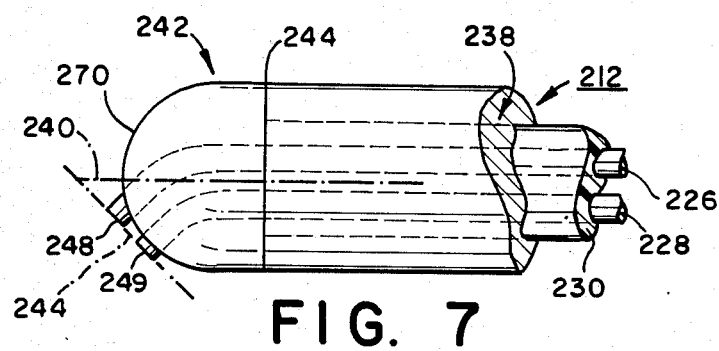
FIG. 7 is a diagrammatic side elevation of a fourth probe assembly tip configuration.

Another envisioned probe assembly variation 212 of the invention is depicted in FIG. 7. The active region 242 at a remote end of a bipolar electrode probe assembly 212 is shown and is formed by a hollow metal tube 238 having an end 244 and a substantially hemispherical insulative material tip 270 extending from the end 244. The metallic tube 238 is not an electrode and is provided only for strength of the probe assembly 212. The tip 270 supports two metal conductors 226 and 228. Each has a tip 248 and 249, respectively, said tips being exposed through the side of the hemispherical surface of the insulative tip 270. Each of the conductors 226 and 228 extends through the hollow interior of the tube 238 to a supporting insulative handle (not depicted) where it is coupled by appropriate means with a bipolar power supply connector (also not depicted) in the manner previously described. The protruding tips 248 and 249 are exposed asymmetrically with respect to the central axis 240 of the tube 238 and hemispherical insulation 270 and lie along axis 244 substantially coplanar with and intersecting axis 240. Axis 244 between electrode tips 248 and 249 also represents the axis of closest approach between the exposed electrode tips 248 and 249. The protruding tips 248 and 249 of the members 226 and 228 are sized, shaped and spaced with respect to one another for optimizing current density in tissue lying between those tips 248 and 249. One of the two tips 248, 249 is envisioned to have a distinct to smaller diameter to increase the current around that electrode. It is envisioned that the hemispherical tip 270 is formed monolithically from an insulative material with a cylindrical sleeve 230 which separates conductors 226 and 228 along the length of 238.

It is further envisioned that an electrically insulative, preferably also friction reducing covering, such as polytetrafluroethylene, is provided along the entire clindrical outer side wall 33 of the outer electrode 28, or at least that remote portion of the tip expected to contact the patient so as to concentrate current flow through the transverse annular end surface 34 of that electrode.

The coating reduces stray currents to the outer electrode disturbing the desired current density around the center electrode and reduces friction, making insertion and removal easier.

The preferred use of the device is in the performing of anterior capsulotomies. In that procedure, a limbal incision is made and the active tip 32 inserted between the anterior capsule and the corneal endothelium. Preferably the anterior capsule surface is wetted with the conventional sterile salt solution. The two electrodes in the active tip of the probe are placed in contact with the anterior capsule surface and a suitable current passed for a length of time sufficient to coagulate a small area of the capsule immediately beneath the active tip. The probe center electrode is moved to a spot adjacent to the coagulated point and the process repeated until a closed curve of desired geometry (i.e. circle, triangle, "D") is made. Typically, a setting of "3" (approximately 3–4 watts) is used with the Grieshaber solid state bipolar power supply unit and with the aforesaid probe employing a nineteen needle gauge size outer electrode, a 0.25 mm inner electrode and 0.7 mm spacing between the electrode ends. The coagulated anterior capsule is extremely friable may be broken by mechanical penetration with the tip of the probe or a cystytome. Once broken away the center portion of the anterior surface within the closed curve of coagulation points can be removed through the limbal incision.

Although a wet field is preferred, a dry field may be used. However, higher voltages may be required.

While preferred and other embodiments of the invention have been described and various modifications thereto suggested, still other modifications and changes would be suggested to one of ordinary skill in the art. The subject invention is therefore not limited to the aforesaid disclosure but rather is defined by the accompanying claims.

We claim:

1. In a coaxial, bi-polar electrode device suitable for opthalmic surgery, the improvement comprising:
   (a) a first tubular electrode having a central axis at a first hollow tubular end thereof;
   (b) a second electrode extending from said hollow tubular end of said first electrode and radially away from said central axis, said second electrode having an outer dimension of about 0.10 mm to about 0.25 mm and having an extreme tip permanently spaced about 0.7 mm or less from said first electrode so as to provide a single axis of closest approach between said electrodes for concentrating current density along said single axis; and
   (c) an insulating sleeve disposed between said first and second electrodes along said central axis.

2. The device of claim 1 wherein said second electrode is disposed to form an angle of approximately 60° to about 90° with said central axis.

3. The device of claim 1 wherein said second electrode is disposed to form an angle of approximately 80° to about 90° with said central axis.

4. The device of claim 3 wherein said extreme tip of said second electrode comprises a surface which is substantially parallel to said central axis.

5. The device of claim 4 wherein said surface is flushed with an outer side wall of said first tubular electrode.

6. The device of claim 3 wherein said extreme tip comprises a tapered end portion.

7. The device of claim 6 wherein said tapered end portion is disposed approximately flush with an outer side wall of said first tubular electrode.

8. The device of claim 1 wherein said extreme tip of said second electrode is permanently spaced about 0.25 mm to about 0.50 mm from said first electrode.

9. A method of performing an anterior capsulotomy procedure comprising:
   (a) providing a co-axial bi-polar electrode device including a first tubular electrode having a central axis at a first hollow tubular end thereof, a second electrode extending from said hollow tubular end of said first electrode and radially away from said central axis, said second electrode having an outer dimension of about 0.10 mm to about 0.25 mm or less and having an extreme tip permanently spaced about 0.7 mm or less from said first electrode so as to provide a single axis of closest approach between said electrodes for concentrating current density along said single axis, said device further having an insulating sleeve disposed between said first and second electrodes along said central axis;
   (b) making a limbal incision in an eye;
   (c) inserting said device between the anterior capsule and the corneal endothelium of said eye; contacting said first and second electrodes with said anterior capsule;
   (d) coagulating a portion of said anterior capsule with said first and second electrodes to form a closed curve; and
   (e) removing a closed curve of coagulated anterior capsule through said limbal incision.

* * * * *